United States Patent
Patel

(10) Patent No.: US 11,533,764 B2
(45) Date of Patent: Dec. 20, 2022

(54) SYSTEMS AND METHODS FOR REMOTELY CONTROLLING A SURGICAL INSTRUMENT OF CONSOLE-BASED SURGICAL SYSTEMS

(71) Applicant: Stryker Corporation, Kalamazoo, MI (US)

(72) Inventor: Tirup Vishnubhai Patel, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 122 days.

(21) Appl. No.: 16/967,954

(22) PCT Filed: Mar. 7, 2019

(86) PCT No.: PCT/US2019/021128
§ 371 (c)(1),
(2) Date: Aug. 6, 2020

(87) PCT Pub. No.: WO2019/173574
PCT Pub. Date: Sep. 12, 2019

(65) Prior Publication Data
US 2021/0385889 A1    Dec. 9, 2021

Related U.S. Application Data

(60) Provisional application No. 62/640,774, filed on Mar. 9, 2018.

(51) Int. Cl.
*H04W 76/14*    (2018.01)
*G16H 40/67*    (2018.01)
(Continued)

(52) U.S. Cl.
CPC ............ *H04W 76/14* (2018.02); *A61B 17/00* (2013.01); *G16H 40/67* (2018.01);
(Continued)

(58) Field of Classification Search
CPC combination set(s) only.
See application file for complete search history.

(56) References Cited

U.S. PATENT DOCUMENTS

| | | |
|---|---|---|
| 6,892,052 B2 | 5/2005 | Kotola et al. |
| 7,565,108 B2 | 7/2009 | Kotola et al. |

(Continued)

FOREIGN PATENT DOCUMENTS

WO    2017009735 A1    1/2017

OTHER PUBLICATIONS

CONMED Linvatec, Arthroscopic Energy Wireless Footswitch Operator's Manual, 2017, 18 pages.
(Continued)

*Primary Examiner* — Cindy Trandai
(74) *Attorney, Agent, or Firm* — Howard & Howard Attorneys PLLC

(57) ABSTRACT

A surgical system and a method of operating a surgical system are disclosed herein. The surgical system comprises a surgical console, a control device, and a dongle. The surgical console operates a surgical device and comprises a connection port. The control device communicates with the surgical console to remotely control the surgical device. The dongle physically couples to the connection port of the surgical console. The control device comprises a first communication device and a radio frequency (RF) reader, and the dongle comprises a second communication device and a passive RF device. The RF reader receives the pairing information from the passive RF device in response to the passive RF device being with a threshold proximity of the RF reader. The first and second communication devices wirelessly connect based on the pairing information, enabling the control device to wirelessly communicate with the surgical console to remotely control the surgical device.

25 Claims, 7 Drawing Sheets

(51) Int. Cl.
*H04W 12/037* (2021.01)
*H04W 12/50* (2021.01)
*A61B 17/00* (2006.01)

(52) U.S. Cl.
CPC ......... *H04W 12/037* (2021.01); *H04W 12/50* (2021.01); *A61B 2017/00199* (2013.01); *A61B 2017/00212* (2013.01); *A61B 2017/00221* (2013.01)

(56) References Cited

U.S. PATENT DOCUMENTS

| | | | |
|---|---|---|---|
| 7,643,798 B2 | 1/2010 | Ljung | |
| 7,781,941 B2 | 8/2010 | Horvath et al. | |
| 7,846,150 B2 | 12/2010 | Hamel et al. | |
| 8,159,370 B2 | 4/2012 | Shields et al. | |
| 8,175,590 B2 | 5/2012 | Hamel et al. | |
| 8,725,082 B2 * | 5/2014 | Seo | G06F 13/4045 455/66.1 |
| 8,774,713 B2 | 7/2014 | Rose et al. | |
| 8,831,509 B2 | 9/2014 | Moosavi et al. | |
| 8,905,317 B1 | 12/2014 | Hsu et al. | |
| 8,937,561 B2 | 1/2015 | Shields et al. | |
| 8,994,509 B2 | 3/2015 | Gottlich | |
| 9,035,741 B2 | 5/2015 | Hamel et al. | |
| 9,050,123 B2 | 6/2015 | Krause et al. | |
| 9,265,518 B2 | 2/2016 | Ware et al. | |
| 9,355,350 B2 | 5/2016 | Hsu et al. | |
| 9,454,896 B2 | 9/2016 | Hocke | |
| 9,496,927 B1 | 11/2016 | Grinberg et al. | |
| 11,257,057 B1 * | 2/2022 | Asmi | G06Q 20/204 |
| 2003/0052547 A1 * | 3/2003 | Fischer | H02J 7/0045 307/154 |
| 2006/0250585 A1 * | 11/2006 | Anderson | G03B 21/10 353/79 |
| 2008/0194300 A1 * | 8/2008 | Rofougaran | G06F 1/3296 455/574 |
| 2008/0262476 A1 | 10/2008 | Krause et al. | |
| 2009/0111378 A1 * | 4/2009 | Sheynman | H04W 4/80 455/41.1 |
| 2010/0123604 A1 | 5/2010 | Shields et al. | |
| 2010/0124366 A1 | 5/2010 | Shields et al. | |
| 2010/0130964 A1 | 5/2010 | Ware et al. | |
| 2012/0271725 A1 * | 10/2012 | Cheng | G06Q 20/202 705/21 |
| 2013/0099902 A1 | 4/2013 | Shields et al. | |
| 2013/0298752 A1 | 11/2013 | Juszkiewicz | |
| 2014/0044435 A1 * | 2/2014 | Kobayashi | H04W 76/14 398/130 |
| 2014/0092054 A1 * | 4/2014 | Ng | G06F 3/0442 345/173 |
| 2014/0148095 A1 | 5/2014 | Smith et al. | |
| 2014/0180110 A1 | 6/2014 | Schmedling | |
| 2014/0241714 A1 * | 8/2014 | Chen | G06F 3/03543 455/39 |
| 2015/0121466 A1 * | 4/2015 | Brands | H04L 63/08 726/4 |
| 2015/0216513 A1 | 8/2015 | Hamel et al. | |
| 2015/0349561 A1 * | 12/2015 | Berggren | H02J 7/007 320/162 |
| 2016/0128678 A1 | 5/2016 | Ware et al. | |
| 2016/0212796 A1 * | 7/2016 | Wang | H04W 12/40 |
| 2016/0294485 A1 * | 10/2016 | Ma | H04W 76/14 |
| 2016/0361662 A1 * | 12/2016 | Karunaratne | G06F 3/038 |
| 2017/0281000 A1 | 10/2017 | Wedekind et al. | |
| 2017/0296107 A1 * | 10/2017 | Reid | A61N 1/3993 |
| 2018/0047014 A1 * | 2/2018 | Maus | G06Q 20/425 |
| 2018/0070199 A1 * | 3/2018 | Buck | H04W 12/64 |
| 2018/0250553 A1 * | 9/2018 | Pendergast | A63B 24/0003 |
| 2019/0034976 A1 * | 1/2019 | Hamedi | G06Q 30/0243 |
| 2019/0102521 A1 * | 4/2019 | Biewer | G16H 80/00 |
| 2019/0238791 A1 * | 8/2019 | Ingle | A61B 1/04 |
| 2021/0251538 A1 | 8/2021 | Muhsin et al. | |

OTHER PUBLICATIONS

CONMED, "Product Catalog—Consoles and Footswitches", 2017, p. 113.
CONMED, "CONMED Announces Full Market Release of the Zen™ Wireless Footswitch System", May 28, 2009, 2 pages.
CONMED, "ZEN Wireless Footswitch (W1000) and ZEN Wireless Footswitch Adapter (W1000) Instruction Manual", Rev. AB, Mar. 2014, 32 pages.
International Search Report for Application No. PCT/US2019/021128 dated Jun. 25, 2019, 5 pages.

* cited by examiner

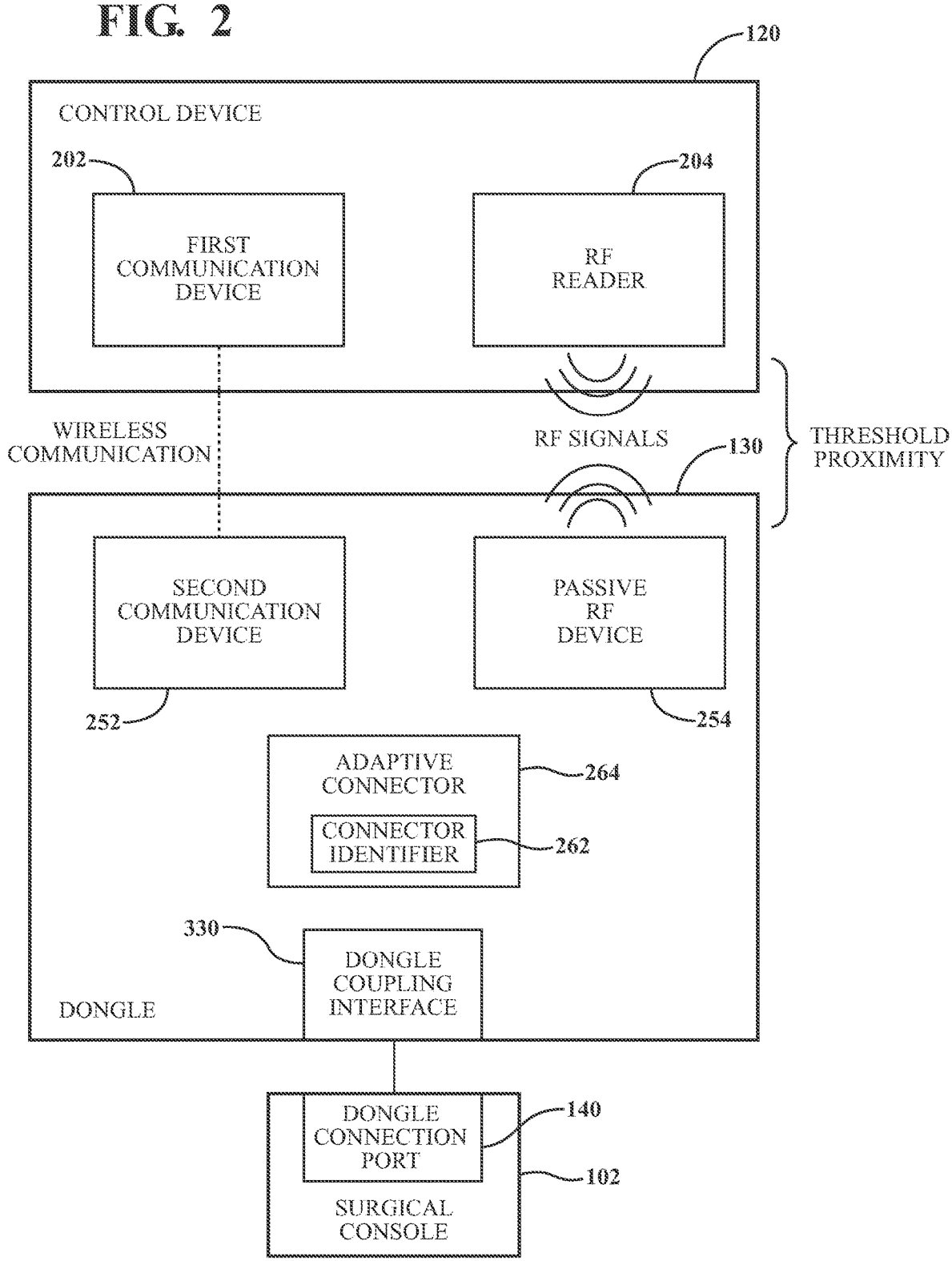

SYSTEMS AND METHODS FOR REMOTELY CONTROLLING A SURGICAL INSTRUMENT OF CONSOLE-BASED SURGICAL SYSTEMS

RELATED APPLICATION

The present application is the National Stage of International Patent Application No. PCT/US2019/021128, filed on Mar. 7, 2019, which claims the benefit of U.S. Provisional Patent Application No. 62/640,774, filed on Mar. 9, 2018, the entire disclosures of which are hereby incorporated by reference.

BACKGROUND

Console-based surgical systems include a surgical console having surgical devices and control devices (e.g., footswitches or handswitches) connected thereto. The surgical devices can be controlled by the control devices through the console. Conventionally, such control devices are physically and directly connected to the console. For example, the control device may include a hard-wired cable and a connector that plugs into the console, thereby allowing the control device to control the surgical device. In such configurations, presence of the cable clutters the operating room or causes a tripping hazard. Moreover, cable management before, during and after any operation requires more time from healthcare personal.

Attempts have been made to control the surgical devices through the console using wireless communication between the control device and the console. Typically, such configurations require a manual and complex pairing process to exchange pairing data between the control device and the console. Such manual pairing requires much time and effort to initiate and execute. For example, identifying and selecting the corresponding device for pairing can be a burdensome process, particularly considering that many other wireless devices are present and discoverable in the local area. Human involvement is needed to select the specific device from all the available devices within range. Manual pairing requires manual entry of verification data for one or more of the devices. Once the device with a specific ID is found, the process may request various security specific data from the devices to authenticate before enabling pairing to exchange the data. Moreover, even if identified and selected, the devices may fail to pair because of technical difficulties associated with manual pairing. The typical manual and complex pairing process involved with wireless communication is not user-friendly and discourages healthcare professionals from using wireless communication between the control device and console.

In some instances, wireless devices may be hard-paired, such that one device is preconfigured to wirelessly communicate solely with a specified device, and vice-versa. One problem with such an approach relates to inventory. In large healthcare facilities, for example, surgical system devices are often mixed and matched, as required by demand in the facility. Hard-paired devices must remain together in inventory to provide utility. If one of the devices is separated and mixed with another system, both devices become inoperable.

Therefore, there remains a need in the art to address at least the aforementioned problems related to wireless communication between surgical consoles and control devices.

SUMMARY OF THE DISCLOSURE

One example surgical system is provided. The surgical system comprises a surgical console, a control device, and a dongle. The surgical console operates a surgical device and comprises a connection port. The control device communicates with the surgical console to remotely control the surgical device. The dongle physically couples to the connection port of the surgical console. The control device comprises a first communication device and a radio frequency (RF) reader and the dongle comprises a second communication device and a passive RF device. The RF reader receives the pairing information from the passive RF device in response to the passive RF device being within a threshold proximity of the RF reader. The first and second communication devices wirelessly connect based on the pairing information, enabling the control device to wirelessly communicate with the surgical console to remotely control the surgical device.

One potential implementation of a method of operating a surgical system is provided. The surgical system comprises a surgical console configured to operate a surgical device, the surgical console comprising a connection port. The surgical system also comprises a control device and a dongle. The control device communicates with the surgical console to remotely control the surgical device, the control device comprising a first communication device and an RF reader. The dongle comprises a second communication device and a passive RF device. The method of operating the surgical system includes a step of establishing a threshold proximity between the passive RF device of the dongle and RF reader of the control device; a step of receiving, with the RF reader of the control device, pairing information from the passive RF device of the dongle in response to the passive RF device and the RF reader being within the threshold proximity; a step of physically coupling the dongle to the connection port of the surgical console; a step of establishing a wireless connection between the first and second communication devices based on the pairing information; and a step of remotely and wirelessly controlling the surgical device with the control device using the wireless connection.

An example surgical system is provided. The surgical system comprises a surgical console, a control device, a first dongle, and a second dongle. The surgical console operates a surgical device and comprises a connection port. The control device communicates with the surgical console to remotely control the surgical device. The first dongle comprises a first communication device and a passive RF device and the second dongle includes a second communication device and an RF reader. One of the first and second dongles physically couples to the connection port of the surgical console and the other one of the first and second dongles physically couples to the connection port of the control device. The RF reader receives the pairing information from the passive RF device in response to the passive RF device being within a threshold proximity of the RF reader. The first and second communication devices wirelessly connect based on the pairing information, enabling the control device to wirelessly communicate with the surgical console to remotely control the surgical device.

One example dongle for a surgical system is provided. The surgical system comprises a surgical console configured to operate a surgical device, the surgical console comprising a connection port. The surgical system also comprises a control device configured to communicate with the surgical console to remotely control the surgical device, the control device comprising a communication device and an RF reader. The dongle comprises a coupling interface, a passive RF device and a communication device. The coupling interface physically couples the dongle to the connection port of the surgical console. The passive RF device is configured to transmit pairing information to the RF reader of the control device in response to the passive RF device being within a threshold proximity of the RF reader. The communication device of the dongle is configured to wirelessly connect to the communication device of the control device based on the pairing information to enable wireless communication between the control device and the surgical console to remotely control the surgical device.

One example communication system for a surgical system is provided. The surgical system comprises a surgical console and a control device. The surgical console operates a surgical device and comprises a connection port. The control device communicates with the surgical console to remotely control the surgical device and comprises a connection port. The communication system comprises a first dongle and a second dongle. The first dongle comprises a first coupling interface configured to physically couple to the connection port of one of the surgical console and the control device, an RF reader, and a first communication device. The second dongle comprises a second coupling interface, a passive RF device, and a second communication device. The second coupling interface is configured to physically couple to the connection port of the other one of the surgical console and the control device, which is not physically coupled to the first coupling interface. The passive RF device transmits pairing information to the RF reader of the first dongle in response to the passive RF device and the RF reader being within a threshold proximity to one another. The second communication device wirelessly connects to the first communication device of the first dongle based on the pairing information to thereby enable the control device to wirelessly communicate with the surgical console to remotely control the surgical device.

Advantages of the surgical systems, methods, dongles, and communication systems will be readily appreciated from the specification.

BRIEF DESCRIPTION OF THE DRAWINGS

Referring now to the drawings, example illustrations are shown in detail. Although the drawings represent examples, the drawings are not necessarily to scale and certain features may be exaggerated or schematic in form to better illustrate and explain a particular aspect of an illustrative example. Any one or more of these aspects can be used alone or in combination with one another. Further, the example illustrations described herein are not intended to be exhaustive or otherwise limiting or restricting to the precise form and configuration shown in the drawings and disclosed in the following detailed description. Example illustrations are described in detail by referring to the drawings as follows:

FIG. 2 is a system block diagram of aspects of the surgical system of FIG. 1A;

DETAILED DESCRIPTION

Figure 1A:
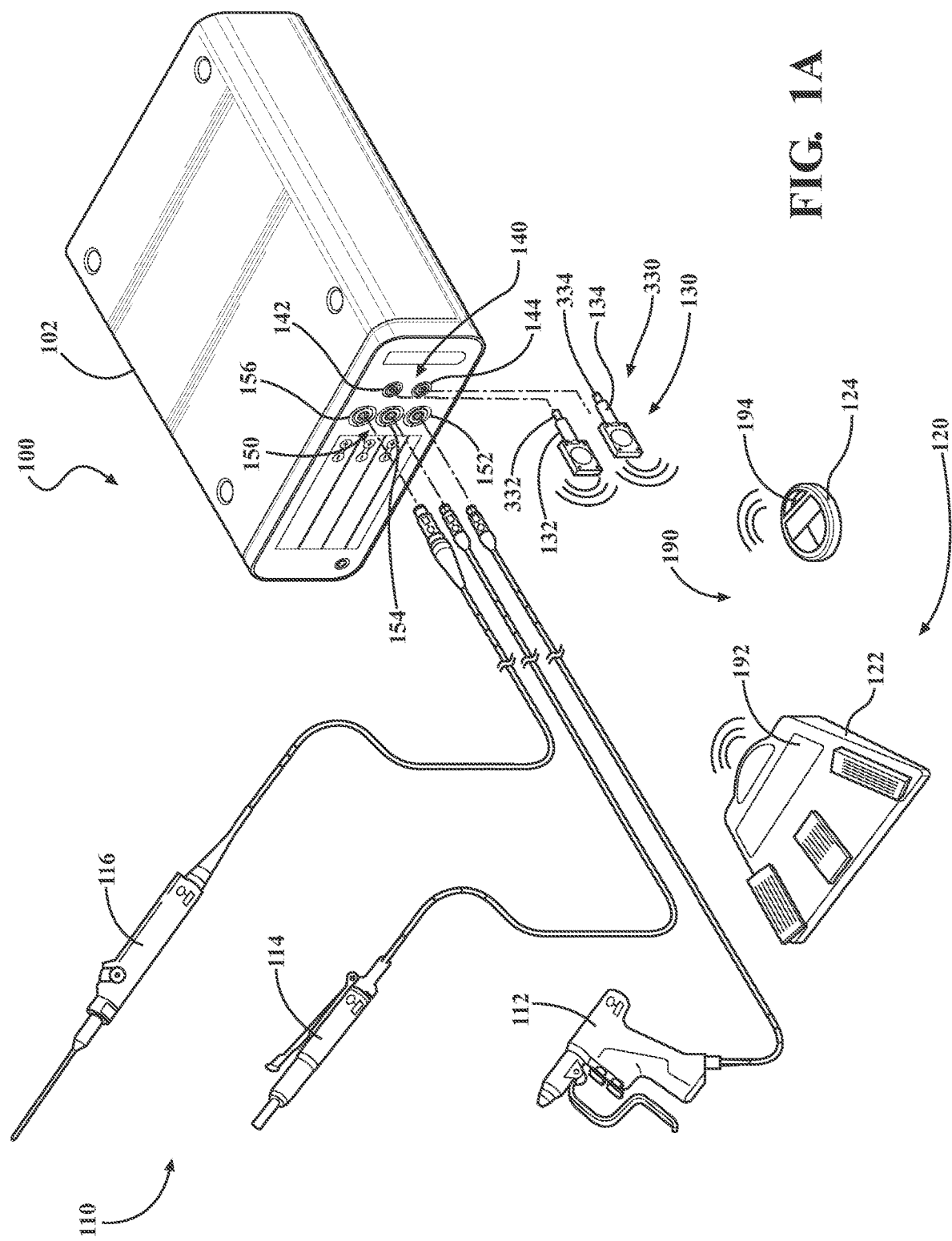
FIG. 1A is an assembly view of an example surgical system comprising a surgical console, a plurality of surgical instruments, a plurality of dongles for connecting to the surgical console, and a plurality of control devices.

Referring to FIG. 1A, one example surgical system 100 is shown. As shown, the surgical system 100 includes a surgical console 102, which is configured to operate a surgical device 110. The surgical device 110 may be one of many surgical devices, such as those illustrated as surgical devices 112, 114, 116 in FIGS. 1A and 1B. Examples of the surgical device 110 are explained in detail below.

The surgical system 100 also includes a control device 120. Control devices 120 may be configured to communicate with the surgical console 102 to remotely control surgical devices 110. In one example, the control devices 120 include a foot-operable control device 122 as shown in FIG. 1A (the foot-operable control device referred to herein as a "footswitch"). In another example, the control devices 120 include a hand-operable control device 124, as shown in FIG. 1A (the hand-operable control device referred to herein as a "handswitch").

Furthermore, the surgical system 100 may include a dongle 130, illustrated as dongles 132, 134. Dongles 130 may be configured to physically couple to a dongle connection port 140 of the surgical console 102, illustrated as connection ports 142, 144. As shown in FIG. 1A, control devices 120 and dongles 130 wirelessly connect, allowing the control devices 120 to wirelessly communicate with the surgical console 102 to remotely control the surgical devices 110.

Figure 1B:
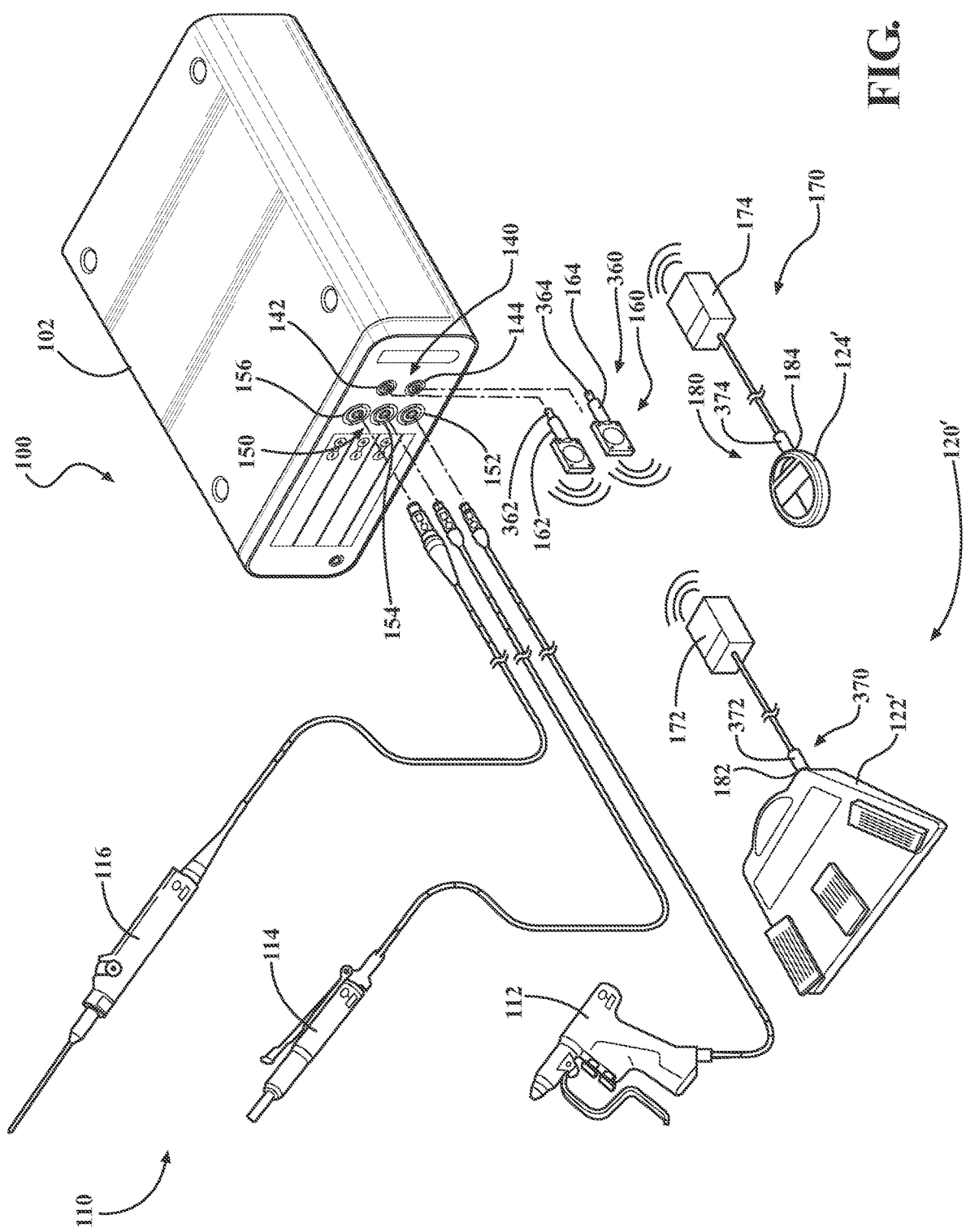
FIG. 1B is an assembly view of another example surgical system comprising a surgical console, a plurality of surgical instruments, a plurality of (first) dongles for connecting to the surgical console, a plurality of control devices, and a plurality of (second) dongles for connecting to the control devices.

Referring to FIG. 1B, another example surgical system 100 is shown. Similar to the surgical system 100 in FIG. 1A, the surgical system 100 in FIG. 1B includes the surgical console 102, which is configured to operate surgical devices 110. However, the example shown in FIG. 1B includes two types of dongles, i.e., first dongles 160 and second dongles 170. The first dongles 160 are illustrated as first dongles 162, 164, and the second dongles 170 are illustrated as second dongles 172, 174. The control devices 120' are illustrated as footswitch 122' and handswitch 124'.

As shown in FIG. 1B, the first dongles 160 may physically couple to dongle connection ports 140 of the surgical console 102. The second dongles 170 physically couple to dongle connection ports 180 of the control devices 120', illustrated as dongle connection ports 182, 184. As shown, the first dongles 160 and the second dongles 170 wirelessly connect, allowing the control devices 120' to wirelessly communicate with the surgical console 102 to remotely control the surgical devices 110.

In some instances, the dongles 130 and the first dongles 160 may be included within the surgical console 102. Such an instance is further described in U.S. Pat. No. 7,846,150 B2, entitled "Apparatus and Method for Synchronizing a Wireless Remote Control to a Central Control Unit so as to Allow Remote Control of a Medical Device over a Secure Wireless Connection," the disclosure of which is hereby incorporated by reference in its entirety. As such, dongles 130 need not be physically coupled to the dongle connection ports 140 to connect to control devices 120. Similarly, the first dongles 160 need not be physically coupled to the dongle connection ports 180 to connect to the second dongles 170.

Herein, components of the surgical systems 100 in FIGS. 1A and 1B may be referred to generically or specifically. For example, "surgical devices 110" may be interpreted as a generic categorization of the specific surgical devices 112, 114, 116. However, the term "surgical devices 110" herein refers to any number of surgical devices and any surgical device that may be operated by the surgical console. In contrast, "surgical devices 112, 114, 116" refer to the surgical devices shown in FIGS. 1A and 1B. Similarly, other components of the surgical systems 110 in FIGS. 1A and 1B may be referred to generically or specifically.

As shown, the example surgical system 100 in FIG. 1A includes one type of dongle, the dongles 130. As such, the example surgical system 100 in FIG. 1A may be referred to herein as a "single-dongle example". In contrast, the example surgical system 100 in FIG. 1B includes two types of dongles, the first dongles 160 and the second dongles 170. As such, the example surgical system 100 in FIG. 2 may be referred to herein as a "double-dongle example". It should be noted that the use of the words "single" and "double" refer to a number of dongle types in each example and not necessarily to a total number of dongles in each example.

As utilized herein, the term "dongle" refers to an auxiliary product that can be inserted into, or otherwise physically coupled to, a host (client or parent) device, such as the surgical console 102 or the control device 120'. In the examples shown in FIGS. 1A and 1B, the dongles 130, 160, 170 enable the control devices 120, 120' to wirelessly connect to the surgical console 102 and control the surgical devices 110. In one example, the dongles 130, 160, 170 are pocket-sized external hardware devices that are distinct from the surgical console 102 or the control device 120'. Hardware and software architecture of the dongles 130, 160, 170 is further described below.

The dongles 130, 160, 170 are provided on-premises at a location of the surgical console 102 or the control device 120'. In other words, the dongles 130, 160, 170 are located at the same location as the surgical console 102 or the control device 120', rather than being remotely located, e.g., across a network. For example, where the surgical console 102 and the control device 120' are located at a surgical site or in an operating room, the dongles 130, 160, 170 are also located at the surgical site or in the operating room. In more specific examples where the control device 120' is located in a sterile field and the surgical console 102 is located in a non-sterile field, the dongle 170 is located in the sterile field and dongles 130, 160 are located in the non-sterile field. As will be understood by the description and examples herein, the dongles 130, 160, 170 are provided on-premises relative to the location of the surgical console 102 or the control device 120' because, in part, dongles 130, 160, 170 and the surgical console 102 or the control device 120' must be physically coupled to each other using dongle connection ports 140, 180.

In some examples, the dongles 130, 160, 170 may include a cable. For example, as shown in FIG. 1B, the second dongles 172, 174 include a cable and a dongle coupling interface 372, 374 for physically coupling to the control device 120'. The cable may be of any appropriate length and may be provided for convenience of physically coupling the dongles 130, 160, 170 to the surgical console 102 or to the control device 120'. Where present, the cable preferably has a short length to avoid obstruction in the operating room.

Furthermore, in the single-dongle example, dongles 130 are not specific to control devices 120. In other words, any dongle 130 may be wirelessly connected to any control device 120. For example, in FIG. 1A, the control device 122 is wirelessly connected to the dongle 132 and the control device 124 is wirelessly connected to the dongle 134. However, in another instance of the single-dongle example, the control device 122 may be wirelessly connected to the dongle 134 and the control device 124 may be wirelessly connected to the dongle 132.

Similarly, in the double-dongle example, the first dongles 160 and the second dongles 170 are not specific to one another. In other words, any first dongle 160 may be wirelessly connected to any second dongle 170. For example, in FIG. 1B, the first dongle 162 is wirelessly connected to the second dongle 172 and the first dongle 164 is wirelessly connected to the second dongle 174. However, in another instance of the double-dongle example, the first dongle 162 may be wirelessly connected to the second dongle 174 and the first dongle 164 may be wirelessly connected to the second dongle 172. Thus, the dongles 130, 160, 170 provide universality and flexibility to establish wireless communication between the control device 120 and the surgical console 102.

It should be noted that the surgical console 102 may be of any suitable shape and size and may include components not shown in FIGS. 1A and 1B or described herein. For example, the surgical console 102 may include displays for displaying information from the surgical devices 110. In yet another example, the surgical console 102 may include visual indicators to indicate successful connection of the surgical devices 110 and/or the dongles 130, 160, 170 and to indicate which control devices 120, 120' are controlling which surgical devices 110. The surgical console 102 may be stationary or mobile. The surgical console 102 may be any other device, such as a robotic manipulator, configured to enable control devices 120 to control surgical devices 110 coupled thereto. The surgical console 102 may be one of a variety of surgical consoles 102. For example, the surgical console 102 may be configured to provide capabilities for ultrasonic aspiration, suction, irrigation, RF ablation or lesioning, drilling, sawing, cutting, milling, imaging, and the like.

The surgical systems 100 may include any suitable number of surgical devices 110, dongles 130, 160, 170, and control devices 120, 120' other than the number shown in FIGS. 1A and 1B.

In the example surgical systems 100 shown in FIGS. 1A and 1B, three examples of the surgical devices 110 are provided for illustrative purposes. The illustrated shapes and other structural features of surgical devices 112, 114, 116 as depicted in FIGS. 1A and 1B are not intended to describe the surgical devices 110 specifically but rather are intended only to convey the general concept that various surgical devices 110 may be used.

The surgical devices 110 may be operated by the surgical console 102 to perform one or more predetermined functions in the treatment or care of a patient. For example, one or more of the surgical devices 110 may include a specialty drill, a high-powered tapered drill, a modular handpiece, a high-speed pencil-grip drill, a pneumatic drill, a drill for intraoperative procedures, a drill for oral surgery, a drill for ENT surgery, a sagittal, oscillating or a reciprocating saw, a microdebrider, an ultrasonic aspirator, electrodes, probes, or any hand-held imaging device, such as an endoscope or camera, and the like.

Electrosurgical devices, ultrasound devices, and other surgical devices 110 may also be employed. Electrosurgical instruments may be of any suitable type, including those that use diathermy with either unipolar or bipolar current (commonly referred to simply as unipolar devices and bipolar devices), and advanced devices such as harmonic scissors and argon beam and laser devices. As another example, surgical devices 110 that are not handheld, such as surgical robots, hospital beds, lighting systems, and cameras, may also be employed.

The various surgical devices 110 may be produced by different manufacturers or be different versions or models of a surgical device 110. Regardless of any such differences, the surgical console 102 enables the control devices 120 to control the surgical devices 110.

Although the surgical devices 110 in FIGS. 1A and 1B are physically coupled to the surgical console 102 via a cable and a connector, the surgical devices 110 may be wirelessly connected to the surgical console 102. For example, the surgical devices 110 may be wirelessly connected to the surgical console 102 using dongles similar to the dongles 130, 160, 170 described herein.

Additionally, while surgical devices 110 are emphasized in this disclosure, other types of medical devices may also be used in place thereof. For example, suitable medical devices that could be used in conjunction with the surgical console 102 include, but are not limited to, patient therapy devices, patient monitoring devices, temperature management systems, respirators, IV systems, battery management systems, robotic devices, heart rate monitors, or any other medical device that may be used in medical procedures or in the provision of medical services to patients. As such, the term "surgical device" may be interchanged with these medical devices throughout this disclosure.

As described, the control devices 120, 120' may be foot-operable control devices. For example, in the examples of FIGS. 1A and 1B, the control devices 120, 120' are illustrated using the footswitch 122 and handswitch 124, respectively. The control devices 120, 120' may include various different configurations to enable an operator to remotely control the surgical devices 110. The control devices 120, 120' may include one or more sensors, such as Hall Effect sensors, magnetic sensors, load cells, pressure sensors, image sensors, inclinometers, or other sensors suitable for generating signals in response to a depression of the footswitch or handswitch.

In other examples, the control devices 120, 120' include hand-operable control (referred to herein as "handswitches"), voice-actuated control, knee-operated control, gesture-control, augmented/mixed reality control, and other types of control that may be actuated by a user and may be suitable for controlling a surgical device 110. In such examples, the control devices 120, 120' may include one or more of the described sensors to generate signals in response to an action of a user of the control devices 120, 120'.

In still other examples, the control devices 120, 120' include a mobile computing device. Such mobile computing devices may include cellular phones, smart phones, laptops, tablets, wearable remote devices, or any other mobile computing device that is suitable for controlling a surgical device 110. For example, the control device 120, 120' may be a tablet customized for surgical applications and including a touchscreen. In such an example, a user of the tablet may operate a surgical device 110 by touching portions of the touchscreen and selecting commands for the surgical device 110.

As shown in FIGS. 1A and 1B, the surgical devices 110 may be physically coupled to the surgical console 102 via surgical device connection ports 150, illustrated as connection ports 152, 154, 156. As shown, surgical device 112 physically couples to the surgical console 102 via the connection port 152. Likewise, surgical devices 114, 116 physically couple to the surgical console 102 via the connection ports 154, 156, respectively. In some examples, the surgical console 102 includes a different number of surgical device connection ports 150. For example, the surgical console 102 may include one, two, four, or any number of surgical device connection ports 150, which may be positioned on any suitable portion of the surgical console 102. Furthermore, in examples where the surgical console 102 does not include surgical device connection ports 150, the surgical devices 110 may be directly coupled to the surgical console 102, without use of surgical device connection ports 150. For example, a cable may be integrally connected to the surgical console 102 and the surgical device 110 may connect to a distal connector port of the cable. Alternatively, the surgical console 102 may not include surgical device connection ports 150 where the surgical devices 110 are wirelessly controlled by the surgical console 102.

As also shown in FIGS. 1A and 1B, dongles 130, 160 may be physically coupled to the surgical console 102 via dongle connection ports 140, and the second dongles 170 may be physically coupled to the control device 120' via dongle connection ports 180. More specifically stated, dongle coupling interfaces 330, illustrated as dongle coupling interfaces 332, 334, may be configured to physically couple to the dongle connection ports 140. Similarly, dongle coupling interfaces 360, illustrated as dongle coupling interfaces 362, 364, of the first dongles 160 may be configured to physically couple to the dongle connection ports 140. Dongle coupling interfaces 370, illustrated as dongle coupling interfaces 372, 374 of the second dongles 170 may be configured to physically couple to the dongle connection ports 180. For example, the dongle coupling interface 332 of the dongle 132 of the single-dongle example (FIG. 1A) may physically couple to the dongle connection port 142 of the surgical console 102. Similarly, dongle coupling interface 374 of the second dongle 174 of the double-dongle example (FIG. 1B) may physically couple to the dongle connection port 184 of the control device 120'. As such, when the dongles 130, 160, 170 are inserted into the surgical console 102 or the control device 120', the dongle coupling interfaces 330, 360, 370 are inserted into the dongle connection ports 140, 180.

The dongle coupling interfaces 330, 360, 370 are configured to mechanically and electrically couple the dongles 130, 160, 170 to the respective host device, i.e., console 102 or control device 120. The dongle coupling interfaces 330, 360, 370 may have any configuration that is configured to securely fit into the connection port 140, 180 of the host device. As such, this mechanical fit secures the dongle 130, 160, 170 to the host device. The dongle coupling interfaces 330, 360, 370 are conductive and enable electrical transmission of communication and power signals between the dongles 130, 160, 170 and the host device. The dongle coupling interfaces 330, 360, 370 may be specifically shaped for the host device, may be one-size-fits all or universally adaptable to connect to any host device.

During hard-wired operation, the control device 120, 120' may connect to the connection ports 140 of the surgical console 102 using a cable and connector. The connector of the cable inserts into the connection port 140. The same connection ports 140 that receive this hard-wired cable connector may also be configured to receive the dongle coupling interfaces 330, 360, 370 of the dongles 130, 160, 170. Thus, in view of the techniques described herein, the cable and connector of the control devices 120, 120' are replaced with the dongles 130, 160, 170, thereby eliminating the need for cable connection between the control device 120, 120' and the surgical console 102.

In some examples, the surgical console 102 and the control device 120' include a different number of dongle connection ports 140, 180, respectively. For example, the surgical console 102 may include one, two, four, or any number of dongle connection ports 140, which may be positioned on any suitable portion of the surgical console 102. Similarly, the control device 120' may include one, two, four, or any number of dongle connection ports 180, which may be positioned on any suitable portion of the control device 120'.

Connection ports 142, 144 of the surgical console 102 for the dongles 130, 160, 170 may have similar or different physical connection interfaces from one another. Connection ports 152, 154, 156 of the surgical console 102 for the surgical devices 110 may have similar or different physical connection interfaces from one another. Similarly connection ports 182, 184 of the surgical console 102 for the first and second dongles 160, 170 may have similar or different physical connection interfaces from one another. Moreover, connection ports 142, 144 for the dongles 130, 160, 170 and connection ports 182, 184 for the first and second dongles 160, 170 may have similar or different physical connection interfaces from the connection ports 152, 154, 156 for the surgical devices 110. For example, the dongles 130, 160, 170 and surgical devices 110 may interchangeably connect to any of the connection ports 140, 150. In other words, the connection ports 140, 150 may receive the connector of the surgical devices 110 and/or the dongle coupling interfaces 330, 360, 370 of the dongles 130, 160, 170.

FIG. 2 illustrates a system block diagram of components of the surgical system 100 of FIG. 1A, and more specifically, the control device 120 of the single-dongle example shown in FIG. 1A. As shown, the control device 120 includes a first communication device 202 and a radio frequency (RF) reader 204. The RF reader 204 may be configured to receive pairing information via RF signals. The first communication device 202 may be configured to wirelessly connect to a device based on the pairing information received by the RF reader 204.

The first communication device 202 and the RF reader 204 may be integrated within the control device 120. In one such example, the control device 120 includes a housing 190, illustrated as housings 192, 194 in FIG. 1A, and the first communication device 202 and the RF reader 204 may be integrated within the housing.

As shown, the dongle 130 includes a second communication device 252 and a passive RF device 254. The passive RF device 254 may be configured to transmit the pairing information via RF signals to the RF reader 204 in response to the passive RF device 254 being within a threshold proximity of the RF reader 204. The second communication device 252 may be configured to wirelessly connect to a device based on the pairing information transmitted by the passive RF device 254.

By design, the passive RF device 254 may be configured to transmit information via RF signals after the passive RF device 254 is powered by RF signals from RF reader 204. The RF signals from the RF reader 204 power the passive RF device 254, enabling the passive RF device 254 to transmit the pairing information via RF signals back to the RF reader 204. In one example, the passive RF device 254 may be a passive RF tag. However, it has been contemplated that the passive RF device 254 may be replaced with other types of RF devices. For instance, the passive RF device 254 may be replaced with an RF device which may be powered internally, such as a battery-assisted RF tag or an active RF tag.

Furthermore, the passive RF device 254 may be configured to transmit the pairing information using RF signals using a frequency defined between 30 kHz and 30 MHz, 400 MHz and 450 MHz, or 860 MHz and 960 MHz. Accordingly, the RF reader 204 of the control device 120 may be configured to receive RF signals with a frequency defined between 30 kHz and 30 MHz, 400 MHz and 450 MHz, or 860 MHz and 960 MHz. Depending on an application of the surgical system 100, it may be advantageous to transmit the pairing information using RF signals with a frequency defined between each of the identified frequency ranges. For example, RF signals with a frequency defined between 30 kHz and 30 MHz have a longer wavelength than RF signals with a frequency defined between 400 MHz and 450 MHz or 860 MHz and 960 MHz. As such, RF signals with a frequency defined between 30 kHz and 30 MHz are able to penetrate metallic substances and liquids more effectively, but have a more limited read range than RF signals with a frequency defined between 400 MHz and 450 MHz or 860 MHz and 960 MHz. Other frequency ranges other than those described herein are possible to operate the passive RF device 254.

Additionally, the RF reader 204 of the control device 120 may be configured to receive the pairing information from the passive RF device 254 in response to the passive RF device 254 being within the threshold proximity of the RF reader 204, as shown in FIG. 2. As such, the passive RF device 254 receives RF signals which are transmitted by the RF reader 204. The RF signals transmitted by the RF reader 204 power the passive RF device 254, enabling the passive RF device 254 to transmit the pairing information to the RF reader 204 via RF signals.

After the RF reader 204 receives the pairing information, the first and second communication devices 202, 252 may be configured to wirelessly connect based on the pairing information. Thus, the first communication device 202 may be configured to transmit control data to the second communication device 252, enabling the control device 120 to wirelessly communicate with the surgical console 102 to remotely control the surgical devices 110.

It should be noted that the first and second communication devices 202, 252 in FIG. 2 may use any communication network or protocol suitable for communicating control signals wirelessly. For example, the first and second communication devices 202, 252 may use WiFi, Infrared, ZigBee, radio waves, cellular signals, any other suitable wireless network, or combinations thereof to communicate wirelessly. It should also be noted that the communication network used by the first and second communication devices 202, 252 may differ from the RF signals used by the passive RF device 254 and the RF reader 204.

The first and second communication devices 202, 252 are configured to operate on a frequency or range that is dictated by the designed communication network or protocol. For example, where the first and second communication devices 202, 252 use Bluetooth for wireless communication, the first and second communication devices 202, 252 may be configured to operate on a frequency between 2.4 and 2.485 GHz. Furthermore, as previously stated, the communication network used by the first and second communication devices 202, 252 may differ from the RF signals used by the passive RF device 254 and the RF reader 204. However, the first and second communication devices 202, 252 may be configured to operate on a frequency which may overlap or be greater than a frequency of operation of the passive RF device 254 and the RF reader 204. For instance, as previously stated, the passive RF device 254 and the RF reader 204 may be configured to transmit and receive RF signals with a frequency defined between 30 kHz and 30 MHz, 400 MHz and 450 MHz, or 860 MHz and 960 MHz. In one example, the first and second communication devices 202, 252 may be configured to operate on a frequency which overlaps the above-stated frequencies, or on a frequency greater than 1 GHz.

In some examples, the first and second communication devices 202, 252 are transceivers. For example, each of the first and second communication devices 202, 252 is capable of receiving and transmitting control data. In another example, the first and second communication devices 202, 252 are different communication devices and may be configured to perform different tasks. For instance, the first communication device 202 may be a dedicated transmitter configured to transmit control data, while the second communication device 252 may be a dedicated receiver configured to receive control data.

The pairing information transmitted by the passive RF device 254 of the dongle 130 and received by the RF reader 204 of the control device 120 may include a unique identification of the dongle 130. The pairing information may also include communication parameters associated with the dongle 130. For example, the communication parameters associated with the dongle 130 may include a bits-per-character, a bits-per-second, a baud rate, parity bits, and start, stop, and mark bits. In other examples, the pairing information includes other communication parameters. For instance, the pairing information may include communication parameters which may be specific to Bluetooth, WiFi, Infrared, ZigBee, radio waves, cellular signals, or any other communication network which the first communication device 202 or the second communication device 252 may use to wirelessly communicate with another device.

In some examples, the pairing information transmitted by the passive RF device 254 of the dongle 130 and received by the RF reader 204 of the control device 120 are encrypted by the dongle 130 and decrypted by the control device 120. Similarly, the control data transmitted by the first communication device 202 of the control device 120 and received by the second communication device 252 of the dongle 130 may be encrypted by the control device 120 and decrypted by the dongle 130. As such, by encrypting and decrypting the pairing information and the control data, the surgical system 100 allows for increased security of the pairing information and the control data. Additionally, the surgical system 100 may ensure that control devices 120 control a correct surgical device 110. Similarly, the surgical system 100 may ensure that surgical devices 110 are controlled by a correct control device 120.

Furthermore, as shown in FIG. 2, the dongle 130 may include a connector identifier 262. The connector identifier 262 is configured to determine a type of communication protocol used by the surgical console 102. As previously stated, the surgical console 102, to which the dongle 130 physically couples, may include a variety of surgical consoles 102, which may receive and transmit data using a variety of communication protocols. For example, the surgical console 102 may use UART, I²C, CAN, 1-Wire, SPI, USB, UNI/O, or any other suitable communication protocol to receive and transmit data. As such, the connector identifier 262 determines the type of communication protocol used by the surgical console 102.

The dongle 130 may also include an adaptive connector 264. After the connector identifier 262 determines the type of communication protocol used by the surgical console 102, the adaptive connector 264 enables the dongle 130 to communicate with the surgical console 102 based on the communication protocol used by the surgical console 102. For example, the surgical console 102 may use UART as the communication protocol to receive and transmit data. As such, after the connector identifier 262 determines that the surgical console 102 uses UART to receive and transmit data, the adaptive connector 264 ensures that the dongle 130 communicates with the surgical console 102 using UART after the dongle coupling interface 330 of the dongle 130 is physically coupled to the dongle connection port 140 of the surgical console 102.

Figure 3:
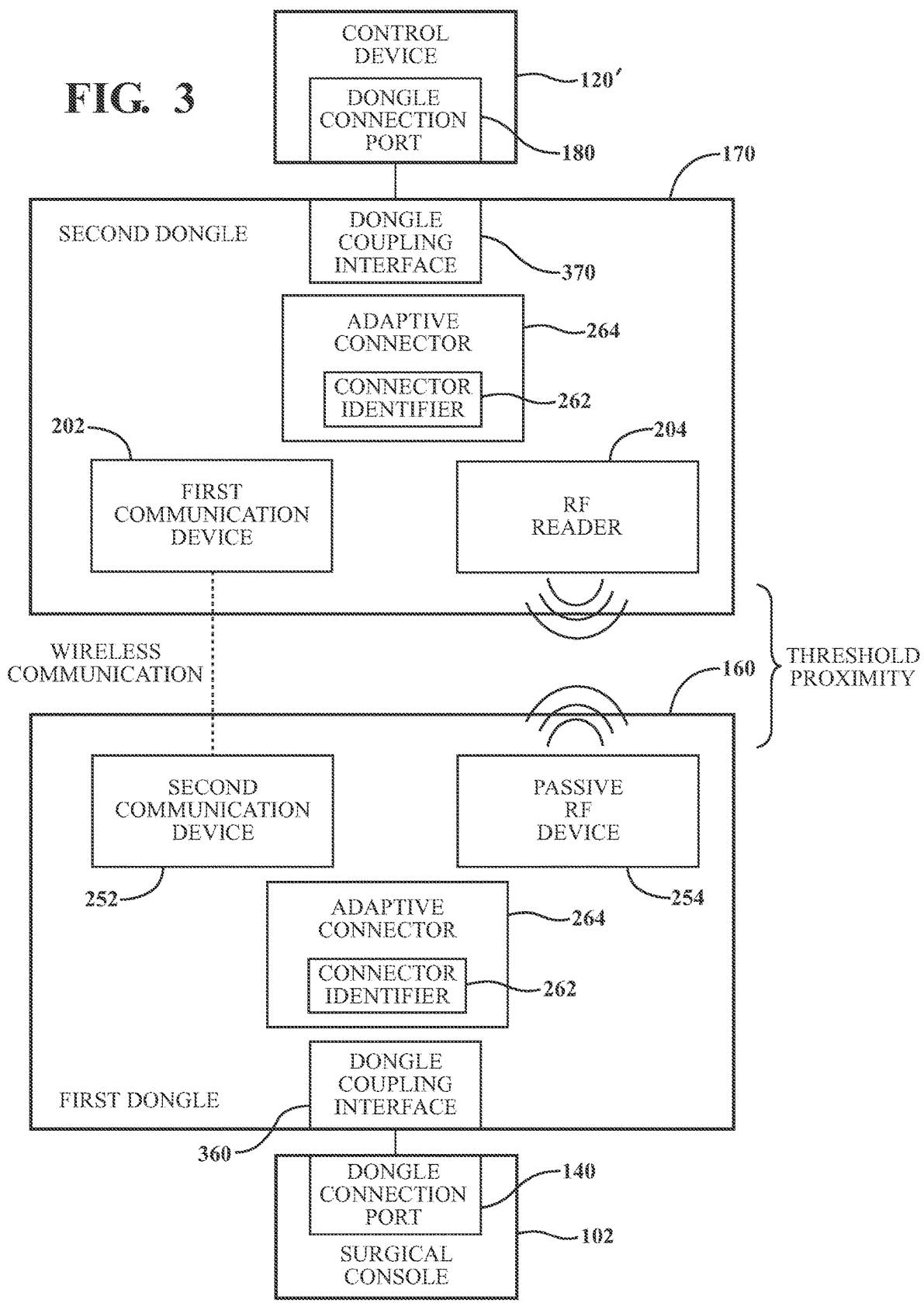
FIG. 3 is a system block diagram of aspects of the surgical system of FIG. 1B.

FIG. 3 illustrates a system block diagram of the surgical system 100 in FIG. 1B, and more specifically, components of the first dongle 160 and the second dongle 170 of the double-dongle example shown in FIG. 1B. As shown in FIG. 3, the first dongle 160 includes the described second communication device 252 and the described passive RF device 254. The second dongle 170 includes the described first communication device 202 and the described RF reader 204. In the double-dongle example, the RF reader 204 of the second dongle 170 receives the pairing information from the passive RF device 254 of the first dongle 160. The first communication device 202 of the second dongle 170 then wirelessly connects to the second communication device 252 of the first dongle 160. As such, the control device 120' wirelessly communicates with the surgical console 102 to remotely control the surgical devices 110.

It should be noted that, while the first dongle 160 is coupled to the surgical console 102 in FIGS. 1B and 3, the first dongle 160 may be physically coupled to the surgical console 102 or to the control device 120'. More specifically, the dongle coupling interface 360 of the first dongle 160 may be physically coupled to the dongle connection port 140 of the surgical console 102 or to the dongle connection port 180 of the control device 120'. Similarly, while the second dongle 170 is coupled to the control device 120' in FIGS. 1B and 3, the second dongle 170 may be physically coupled to the surgical console 102 or to the control device 120'. More specifically, the dongle coupling interface 370 of the second dongle 170 may be physically coupled to the dongle connection port 140 of the surgical console 102 or to the dongle connection port 180 of the control device 120'.

The arrangement of the first and second dongles 160, 170 may be interchangeable with respect to what host device (e.g., surgical console 102, control device 120') the first and second dongles 160, 170 connect. Thus, one dongle 160, 170 connects to one host device 102, 120' while the other dongle 160, 170 connects to the other host device 102, 120'. In other words, if the first dongle 160 is physically coupled to the surgical console 102, then the second dongle 170 is physically coupled to the control device 120'. Similarly, if the first dongle 160 is physically coupled to the control device 120', then the second dongle 170 is physically coupled to the surgical console 102.

Additionally, in the double-dongle example, the pairing information is transmitted by the passive RF device 254 of the first dongle 160 and received by the RF reader 204 of the second dongle 170. As such, the pairing information may include a unique identification of the first dongle 160, which includes the passive RF device 254. The pairing information may also include communication parameters associated with the first dongle 160. As such, in the double-dongle example, the pairing information transmitted by the passive RF device 254 and received by the RF reader 204 may be encrypted by the first dongle 160 and decrypted by the second dongle 170.

Furthermore, in the double-dongle example, the communication device 202, 252 which is physically coupled to the control device 120' transmits the control data. The communication device 202, 252 which is physically coupled to the surgical console 102 receives the control data. As such, in an instance of the double-dongle example where the first dongle 160 is coupled to the surgical console 102 and the second dongle 170 is coupled to the control device 120', the second dongle 170 encrypts the control data and the first dongle 160 decrypts the control data. In an instance of the double-dongle example where the second dongle 170 is coupled to the surgical console 102 and the first dongle 160 is coupled to the control device 120', the first dongle 160 encrypts the control data and the second dongle 170 decrypts the control data.

Also shown in FIG. 3, the first dongle 160 and the second dongle 170 may each include the adaptive connector 264 and the connector identifier 262. As previously stated, the first and second dongles 160, 170 may physically couple to the control device 120' and to the surgical console 102. Also previously stated, the control device 120' may be a variety of control devices and the surgical console 102 may be a variety of surgical consoles. Furthermore, the variety of control devices and the variety of surgical consoles may use different communication protocols to receive and transmit data. As such, the connector identifiers 262 of the first and second dongles 160, 170 determine the communication protocols used by the control device 120' and the surgical console 102. Thus, the adaptive connectors 264 of the first and second dongles 160, 170 enable the first and second dongles 160, 170 to communicate with the control device 120' and with the surgical console 102 based on the communication protocols. This further adds to the universality and adaptability of the double-dongle configuration.

Figure 4:
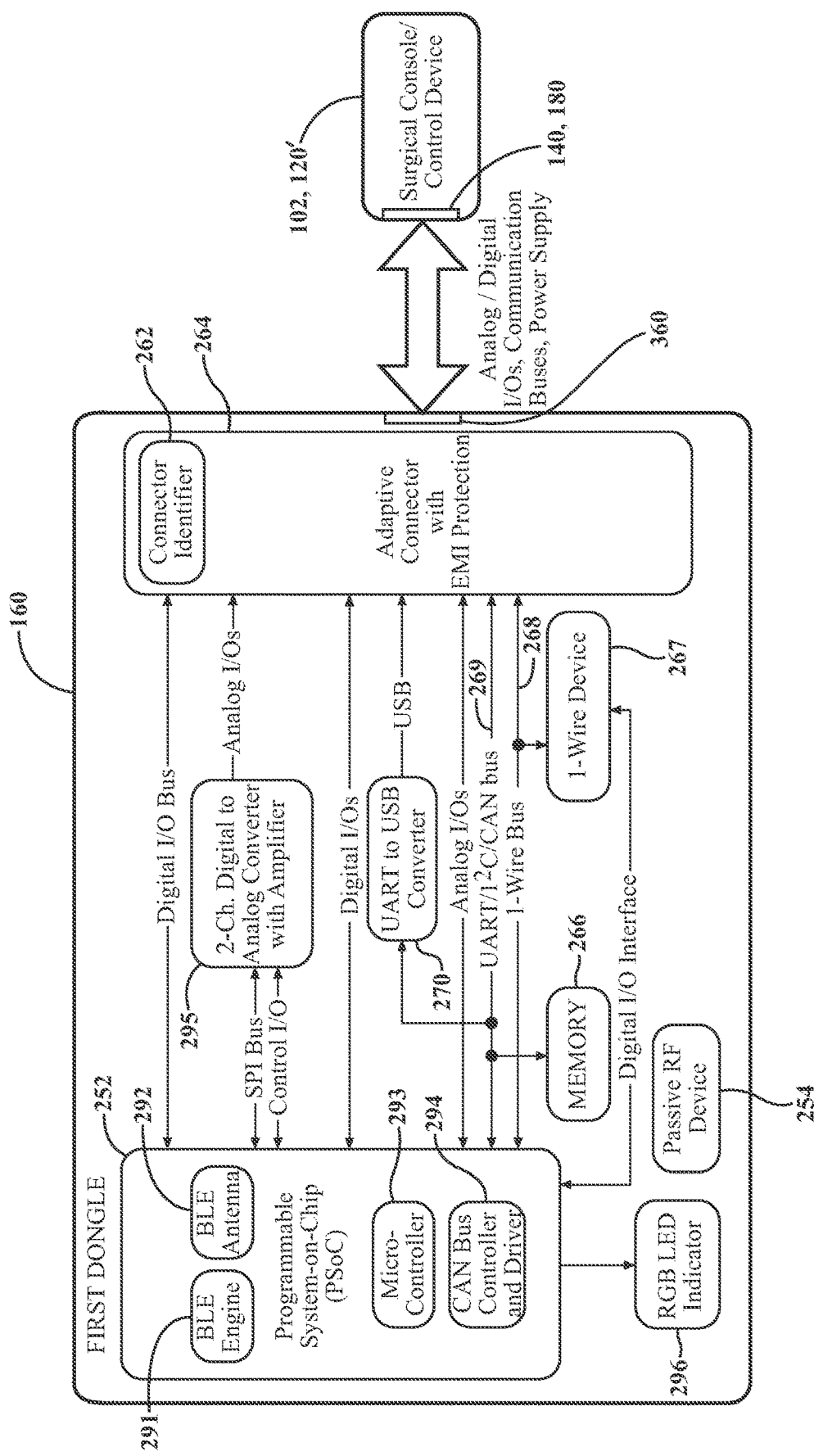
FIG. 4 is a block diagram of example components of the first dongle.
Figure 5:
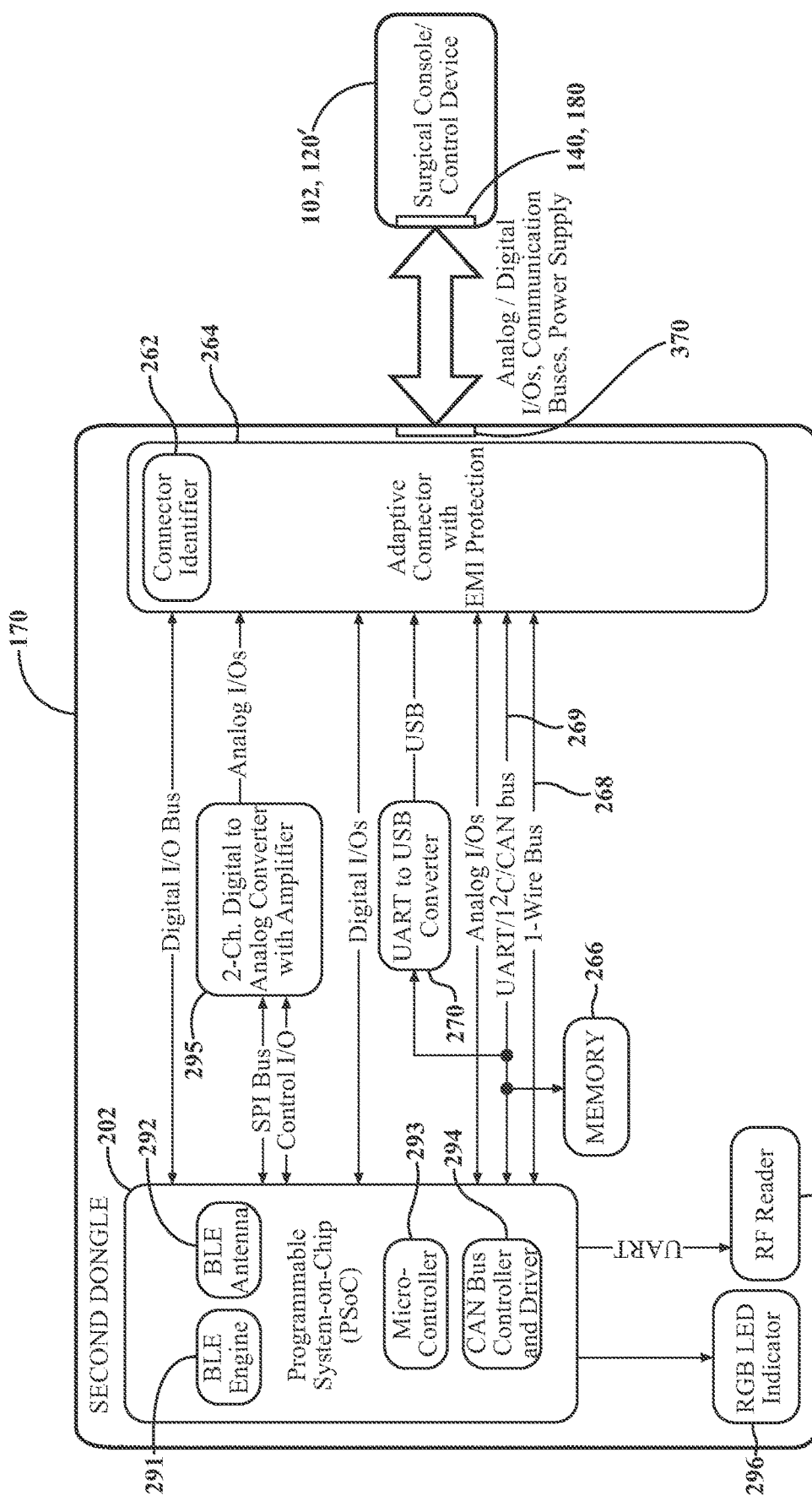
FIG. 5 is a block diagram of example components of the second dongle.

FIGS. 4 and 5 illustrate an example system architecture of the first dongle 160 and the second dongle 170, respectively, of the double-dongle example. Furthermore, for simplicity, while dongle 130 of the single-dongle example is not shown, it is contemplated that the second dongle 170 is similar to dongle 130. For example, both the dongle 130 and the second dongle 170 include the first communication device 202, the RF reader 204, the connector identifier 262, and the adaptive connector 264. However, while the second dongle 170 may be physically coupled to the surgical console 102 or the control device 120', the dongle 130 may be physically coupled to the control device 120. As such, any components of the second dongle 170 shown in FIG. 5 and described herein may be applied to the dongle 130.

It should again be noted that, as shown in FIGS. 4 and 5, the first and second dongles 160, 170 may be physically coupled to the surgical console 102 or to the control device 120'. However, while the first and second dongles 160, 170 may be physically coupled to the surgical console 102 or to the control device 120', when the first dongle 160 or the second dongle 170 is physically coupled to the dongle connection port 140 of the surgical console 102, the other of the first dongle 160 or the second dongle 170 is physically coupled to the dongle connection port 180 of the control device 120'. Therefore, if the first dongle 160 is physically coupled to the surgical console 102, then the second dongle 170 is physically coupled to the control device 120'. Similarly, if the first dongle 160 is physically coupled to the control device 120', then the second dongle 170 is physically coupled to the surgical console 102.

In FIGS. 4 and 5, the first and second communication devices 202, 252 are Programmable System-on-Chip (PSoC) integrated circuits. As shown, the PSoC integrated circuits include a Bluetooth Low Energy (BLE) engine 291 and a BLE antenna 292. As such, the PSoC integrated circuit may communicate wirelessly with other devices using Bluetooth. Furthermore, the PSoC integrated circuit includes a microcontroller 293, which may control the BLE engine 291 and the BLE antenna 292 and other components of the PSoC integrated circuit. The microcontroller 293 may also control inputs and outputs of the PSoC integrated circuit, which are shown in FIGS. 4 and 5 and described below. The PSoC integrated circuit also includes a Controller Area Network (CAN) bus controller and driver 294, which allows the PSoC integrated circuit to receive and transmit CAN messages.

While the first and second communication devices 202, 252 are illustrated as PSoC integrated circuits, the first and second communication devices 202, 252 may be any other circuits suitable for wireless communication, such as ASIC, SOC, etc. In other examples, the first and second communication devices 202, 252 may be any device capable of wirelessly communicating with another device. In such examples, the first and second communication devices 202, 252 may include a controller, or a controller may be coupled to the first and second communication devices 202, 252. Furthermore, while the PSoC integrated circuits include the BLE engine 291 and the BLE antenna 292 for communicating wirelessly with other devices using Bluetooth, the first and second communication devices 202, 252 may communicate with other devices using any other suitable wireless network, such as WiFi, Infrared, ZigBee, radio waves, cellular signals, or combinations thereof.

Additionally, FIGS. 4 and 5 illustrate that the first and second dongles 160, 170 may be configured to receive power from the surgical console 102 and the control device 120'. In some examples, the dongles 130, 160, 170 do not include an internal power supply. As such, the dongles 130, 160, 170 and some components thereof, such as the first and second communication devices 202, 252, may be powered by the surgical console 102 through the dongle connection port 140 or by the control device 120' through the dongle connection port 180. In such examples, operation of some components of the dongles 130, 160, 170 may occur after the dongles 130, 160, 170 are physically coupled to the surgical console 102 or the control device 120'. For example, the second communication device 252 of the first dongle 160 may wirelessly connect to the first communication device 202 of the second dongle 170 after the first dongle 160 is physically coupled to the surgical console 102. In another example, the second communication device 252 of the dongle 130 may wirelessly connect to the first communication device 202 of the control device 120 after the dongle 130 is physically coupled to the surgical console 102. However, it should be noted that the passive RF device 254 of the dongle 130 and the first dongle 160 may be powered by outside sources, such as the RF reader 204, and may therefore operate before the dongle 130 or the first dongle 160 are physically coupled.

FIGS. 4 and 5 also illustrate inputs and outputs of the first and second communication devices 202, 252 and other components of the first and second dongles 160, 170. As shown, the first and second communication devices 202, 252 and the adaptive connector 264 share digital I/Os, as well as a UART/I²C/CAN bus 269 and a 1-Wire bus 268. As such, the first and second communication devices 202, 252 may communicate with the surgical console 102 and the control device 120' using a variety of data types. For example, referring to FIG. 5, the first communication device 202 may communicate serial data with the RF reader 204 via a UART bus. In another example where the surgical console 102 communicates via analog data, the first and second communication devices 202, 252 are configured to transfer digital SPI bus data and digital control I/O data to the surgical console 102 by converting the digital SPI bus data and the digital control I/O data to analog data using a 2-channel digital to analog converter with amplifier 295 and transferring the data using Analog I/Os. Similarly, the first and second communication devices 202, 252 are configured to receive analog data from the surgical console 102 after the analog data has been converted to digital data using the 2-channel digital to analog converter with amplifier 295. In one such example, where a battery life of the dongle 130, 160, 170 is received by the surgical console 102 as analog data, the battery life is converted and communicated from the first or second communication device 202, 252 to the surgical console 102 via the 2-channel digital to analog converter with amplifier 295.

It should be noted that the dongles 130, 160, 170 may include different connections than or may omit some of the connections shown in FIGS. 4 and 5. For example, the first or second communication device 202, 252 may be an integrated circuit other than a PSoC integrated device. As such, the first or second communication devices 202, 252 may include inputs and outputs that vary from the inputs and outputs of the first and second communication devices 202, 252 shown in FIGS. 4 and 5. For instance, if the first or second communication device 202, 252 is an integrated circuit other than a PSoC integrated device, the 2-channel digital to analog converter with amplifier 295 may not be required. Additionally, the UART/I²C/CAN bus 269 and the 1-Wire bus 268 may be omitted or replaced with a bus for a different communication protocol.

In FIGS. 4 and 5, the adaptive connector 264 is coupled to a UART/I²C/CAN bus 269 and a 1-Wire bus 268. As such, the adaptive connector 264 in FIGS. 4 and 5 may enable the first and second dongles 160, 170 to communicate with the surgical console 102 or the control device 120' using UART, I²C, CAN, or 1-Wire. For example, the surgical console 102 may use UART, I²C, CAN, 1-Wire, SPI, USB, UNI/O, or any other suitable communication protocols. For example, the connector identifier 262 of the first dongle 160 determines that the communication protocol used by the surgical console 102 to receive and transmit data is 1-Wire. Accordingly, the adaptive connector 264 enables the first dongle 160 to communicate with the surgical console 102 by transmitting data to the surgical console 102 from the 1-Wire bus 268.

The adaptive connector 264 may also be configured to communicate using communication protocols other than UART, I²C, CAN, and 1-Wire, such as SPI, USB, or UNI/O. For example, in FIGS. 4 and 5, the adaptive connector 264 may be configured to communicate using USB. As such, the first and second dongles 160, 170 include a UART to USB converter 270. Furthermore, the first and second dongles 160, 170 may include a specific bus for each communication protocol or may include a bus for different groupings of communication protocols. For instance, the first and second dongles 160, 170 may include a UART bus, an I²C bus, a CAN bus, a UART/I²C bus, a UART/CAN bus, or an I²C/CAN bus instead of the UART/I²C/CAN bus 269.

Furthermore, as shown in FIGS. 4 and 5, the first and second dongles 160, 170 may include memory 266. In FIGS. 4 and 5, the memory 266 is coupled to the UART/I²C/CAN bus 269. It should be noted that the memory 266 may be coupled to other components of the first and second dongles 160, 170. For example, the memory 266 may be coupled to the digital I/Os of the first and second dongles 160, 170. Furthermore, the memory 266 may be any memory suitable for storage of data and computer-readable instructions. For example, the memory 266 may be a local memory or an external memory embodied as random access memory (RAM), non-volatile RAM (NVRAM), flash memory, or any other suitable form of memory.

In FIG. 4, a 1-Wire device 267 is coupled to the second communication device 252 and to the 1-Wire bus 268. In one example, the 1-Wire device 267 may be a 1-Wire memory, such as local memory or an external memory embodied as random access memory (RAM), non-volatile memory (e.g., a 1-Wire EEPROM or a 1-Wire NVSRAM), flash memory, or any other suitable form of memory. The 1-Wire memory may be configured to store a configuration of the surgical console 102 or the control device 120'. In another example, the 1-Wire device 267 may be a 1-Wire sensor, such as a temperature, current, or voltage sensor. The 1-Wire device 267 may also be a 1-Wire time counter or a 1-Wire battery monitor.

Additionally, some components of the first and second dongles 160, 170 shown in FIGS. 4 and 5 may be omitted. For example, in FIGS. 4 and 5, the first and second dongles 160, 170 include an RGB LED Indicator 296. However, in other examples, the first and second dongles 160, 170 may omit the RGB LED Indicator 296. Similarly, in some examples of the first and second dongles 160, 170, the memory 266 or the 1-Wire device 267 may be omitted. As another example, the UART/I²C/CAN bus 269 or the 1-Wire bus 268 may be omitted.

The microcontroller 293 of the first and second dongles 160, 170 is configured to control, manage or otherwise execute any of the aforementioned capabilities of the first and second dongles 160, 170. For example, such capabilities include, but are not limited to, pairing using the RF reader 204, connector identification using the connector identifier 262, bus communication adaptation using the adaptive connector 264, control signal transmission using the first and second communication devices 202, 252, operation of the indicator 296, retrieval and saving of data from the memory 266 or the 1-Wire device 267 (in instances where the 1-Wire device 267 is a 1-Wire memory), or any other operation triggered by the host device (surgical console 102, control device 120'), and the like.

Figure 6:
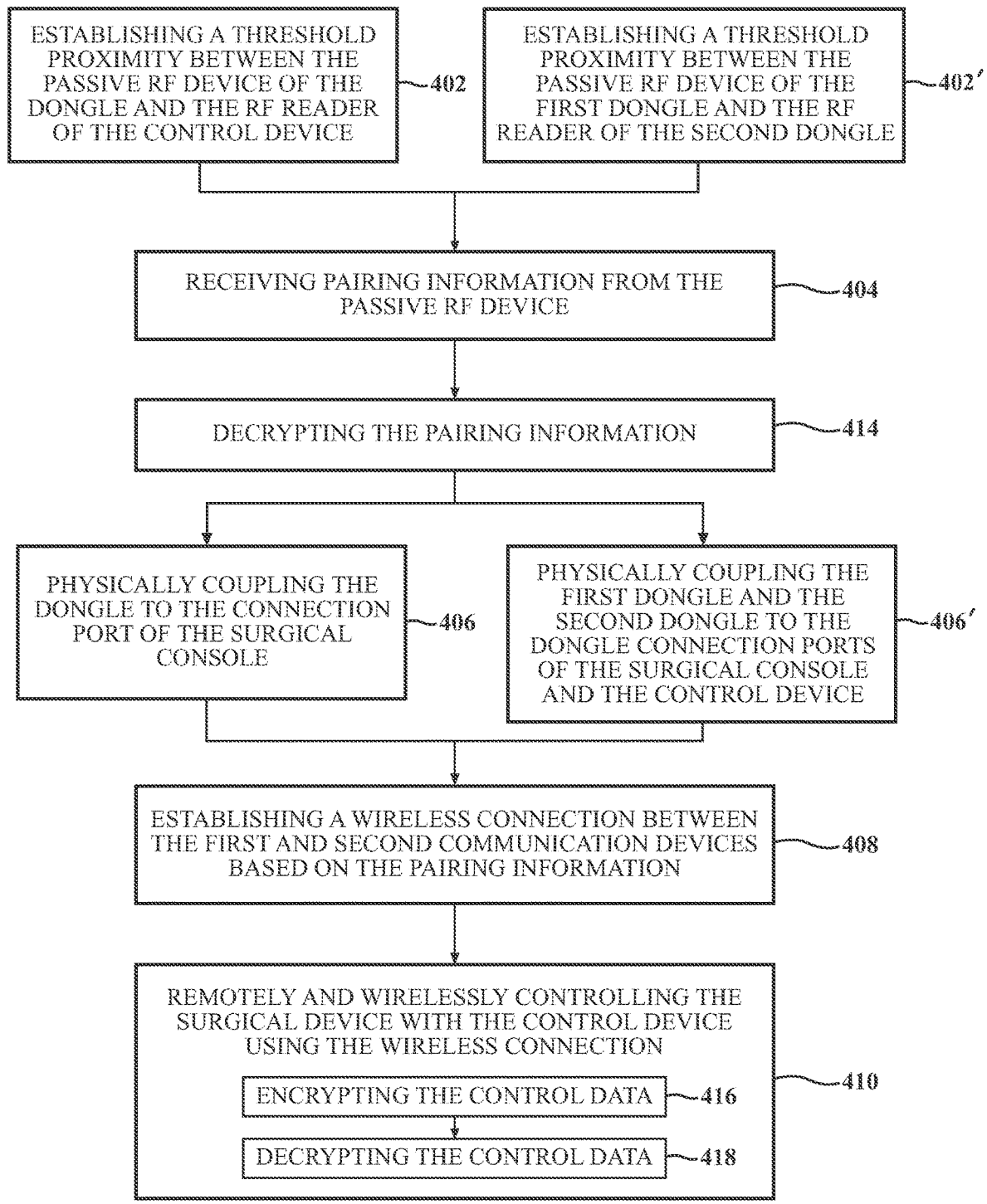
FIG. 6 is a flowchart of a method of operating a surgical system.

A method of operating the surgical system 100 is shown in FIG. 6. As shown, the method includes a step 402 of establishing the threshold proximity between the passive RF device 254 of the dongle 130 and the RF reader 204 of the control device 120 or a step 402' of establishing the threshold proximity between the passive RF device 254 of the first dongle 160 and the RF reader 204 of the second dongle 170; a step 404 of receiving the pairing information from the passive RF device 254; a step 406 of physically coupling the dongle 130 to the dongle connection port 140 of the surgical console 102 or a step 406' of physically coupling the first dongle 160 and the second dongle 170 to the dongle connection port 140 of the surgical console 102 and to the dongle connection port 180 of the control device 120'; a step 408 of establishing a wireless connection between the first communication device 202 and the second communication device 252 based on the pairing information; and a step 410 of remotely and wirelessly controlling the surgical device 110 using the wireless connection.

In the single-dongle example, the method includes step 402. During step 402, the threshold proximity is established between the passive RF device 254 of the dongle 130 and the RF reader 204 of the control device 120. In the double-dongle example, the method includes step 402'. During step 402', the threshold proximity is established between the passive RF device 254 of the first dongle 160 and the RF reader 204 of the second dongle 170.

In both the single-dongle and the double-dongle examples, the threshold proximity may be defined as a distance between the passive RF device 254 and the RF reader 204 that allows the RF reader 204 to receive the pairing information from the passive RF device 254. As previously stated, the passive RF device 254 may be configured to transmit the pairing information using RF signals with a variety of frequencies, which may affect a read range of the RF signals. For example, where the pairing information is transmitted using RF signals with a lower frequency, and thus a longer wavelength, the RF signals have a larger read range, allowing for a greater threshold proximity. Therefore, the threshold proximity may vary according to the frequency of the RF signals. For example, the threshold proximity may be on an order of centimeters or inches. In other examples, the threshold proximity may be on an order of feet or meters. In still other examples, the threshold proximity may be greater than 50 feet. In yet another example, threshold proximity may require a proximity "tapping" between devices that include the passive RF device 254 and the RF reader 204.

In one example, the control device 120 may be disposed in a sterile field and the surgical console 102 may be disposed in a non-sterile field. In such an example, step 402 may include a step of moving the dongle 130 into the sterile field to establish the threshold proximity between the passive RF device 254 of the dongle 130 and the RF reader 204 of the control device 120, or a step of moving the control device 120 into the non-sterile field to establish the threshold proximity between the passive RF device 254 of the dongle 130 and the RF reader 204 of the control device 120. Similarly, in another example, the control device 120' may be disposed in a sterile field and the surgical console 102 may be disposed in a non-sterile field. In such an example, step 402 may include a step of moving the first or second dongle 160, 170 into the sterile or non-sterile field to establish a threshold proximity between the passive RF device 254 of the first dongle 160 and the RF reader 204 of the second dongle 170.

Furthermore, in the previously described examples where the passive RF device 254 is powered by RF signals from the RF reader 204, the passive RF device 254 is powered during step 402. However, it has been contemplated that the passive RF device 254 may be replaced with an RF device which may be powered internally, such as a battery-assisted RF tag or an active RF tag. In such examples, the battery-assisted RF tag or the active RF tag may be powered prior to step 402.

After the threshold proximity is established between the passive RF device 254 and the RF reader 204, the passive RF device 254 transmits the pairing information to the RF reader 204 during step 404. In the single-dongle example, the passive RF device 254 of the dongle 130 transmits pairing information to the RF reader 204 of the control device 120. In the double-dongle example, the passive RF device 254 of the first dongle 160 transmits pairing information to the RF reader 204 of the second dongle 170.

During step 408, the wireless connection is established between the first and second communication devices 202, 252 based on the pairing information received from the passive RF device 254. In the single-dongle example, the wireless connection is established between the first communication device 202 of the control device 120 and the second communication device 252 of the dongle 130. In the double-dongle example, the wireless connection is established between the first communication device 202 of the second dongle 170 and the second communication device 252 of the first dongle 160.

In some examples, the method shown in FIG. 6 may include a step of encrypting the pairing information and a step 414 of decrypting the pairing information. In the single-dongle example, the dongle 130, which includes the passive RF device 254, may encrypt the pairing information; and the control device 120, which includes the RF reader 204, may decrypt the pairing information during step 414. In the double-dongle example, the first dongle 160, which includes the passive RF device 254, may encrypt the pairing information; and the second dongle 170, which includes the RF reader 204, may decrypt the pairing information.

It should be noted that encryption of the pairing information may occur at any time prior to step 404, when the pairing information is transmitted. For example, the pairing information may be encrypted at a time of manufacture of the passive RF device 254. In another example, the pairing information may be encrypted after the passive RF device 254 is powered. For instance, the pairing information may be encrypted after the passive RF device 254 is powered by RF signals from the RF reader 204 during step 402.

Furthermore, step 414 may occur at any time after step 404, the step of receiving the pairing information from the passive RF device 254, and prior to step 408, the step of establishing a wireless connection between the first and second communication devices 202, 252. Otherwise stated, the step 414 of decrypting the pairing information with the RF reader 204 may occur after the pairing information is received by the RF reader 204 during step 404, but before establishing the wireless connection between the first and second communication devices 202, 252 based on the pairing information during step 408.

After step 414, the method proceeds to step 406 in the single-dongle example. During step 406, the dongle 130 is physically coupled to the dongle connection port 140 of the surgical console 102. In one example of step 406, the control device 120 is disposed in a sterile field and the surgical console 102 may be disposed in a non-sterile field. In such an example, step 406 of physically coupling the dongle 130 to the dongle connection port 140 of the surgical console 102 may include a step of moving the dongle 130 into the non-sterile field.

The method proceeds to step 406' in the double-dongle example. During step 406', the first dongle 160 and the second dongle 170 are physically coupled to the dongle connection ports 140, 150 of the surgical console 102 and the control device 120'. In one instance of the double-dongle example (shown in FIG. 1B), the second dongle 170 is physically coupled to the dongle connection port 180 of the control device 120' and the first dongle 160 is physically coupled to the dongle connection port 140 of the surgical console 102 during step 406'. In another instance of the double-dongle example, the second dongle 170 is physically coupled to the dongle connection port 140 of the surgical console 102 and the first dongle 160 is physically coupled to the dongle connection port 180 of the control device 120' during step 406'.

It should be noted that, in FIG. 6, steps 406, 406' are illustrated as occurring prior to step 408. However, steps 406, 406' may occur concurrent to or after step 408 (as well as prior to step 408). In other words, the wireless connection may be established between the first and second communication devices 202, 252 prior to the dongles 130, 160, 170 being physically coupled to the surgical console 102 or the control device 120' via the dongle connection ports 140, 180.

This may occur in examples where the dongles 130, 160, 170, and thus the first and second communication devices 202, 252, are powered internally or are powered prior to being physically coupled to the surgical console 102 or to the control device 120'. However, the dongles 130, 160, 170 and thus, the first and second communication devices 202, 252, may be powered by the surgical console 102 and/or the control device 120' via the dongle connection ports 140, 180. In such examples, steps 406, 406' may occur prior to step 408.

During step 410, the surgical device 110 is remotely controlled by the control device 120 using the wireless connection. In some examples, step 410 may include a step 416 of encrypting the control data and a step 418 of decrypting the control data. In the single-dongle example, the control device 120 may encrypt the control data and the dongle 130 may decrypt the control data. In the double-dongle example, the dongle 160, 170 physically coupled to the control device 120' may encrypt the control data, and the dongle 170, 160 physically coupled to the surgical console 102 may decrypt the control data.

The above-described surgical systems, dongles, communication systems and methods create a more robust surgical environment. By remotely controlling the surgical devices 110 using control devices 120, 120', the control devices 120, 120' no longer require cables and connectors, which clutter the workspace and create obstacles in surgical environments.

Furthermore, the above-described systems and methods disclose a quick and user-friendly means of establishing the wireless connection between the first and second communication devices 202, 252. In the system and methods described above, the pairing information is received by the RF reader 204 by simply establishing the threshold proximity between the RF reader 204 and the passive RF device 254. The wireless connection between the first and second communication devices 202, 252 is then automatically established using this pairing information. By automatically establishing the wireless connection, the systems and methods discussed herein do not require a user to manually provide the pairing information to the first and second communication devices 202, 252. As such, the wireless connection between the first and second communication devices 202, 252 is established in a quick and user-friendly way, minimizing errors from users.

Additionally, the systems and methods disclosed herein simplify inventory management of the components of the surgical system 100. As previously described, any dongle 130 may be wirelessly connected to any control device 120 and any first dongle 160 may be wirelessly connected to any second dongle 170. Therefore, from an inventory management perspective, dongles 130 need not be paired with a specific control device 120 and first dongles 160 need not be specifically paired to a second dongle 170. Furthermore, the dongles 130, 160, 170 may communicate with a variety of surgical consoles 102 due to the connector identifier 262 and the adaptive connector 264 of the dongles 130, 160, 170. Therefore, from an inventory management perspective, the dongles 130, 160, 170 need not be paired with specific surgical consoles 102. In this way, dongles 130, 160, 170 are easily replaced and inventories of the dongles 130, 160, 170 are easily managed.

It will be further appreciated that the terms "include," "includes," and "including" have the same meaning as the terms "comprise," "comprises," and "comprising."

Several examples have been discussed in the foregoing description. However, the examples discussed herein are not intended to be exhaustive or limit the disclosure to any particular form. The terminology which has been used is intended to be in the nature of words of description rather than of limitation. Many modifications and variations are possible in light of the above teachings and the disclosure may be practiced otherwise than as specifically described.

The invention claimed is:

1. A surgical system comprising:
   a surgical console configured to operate a surgical device and comprising a connection port;
   a control device configured to communicate with the surgical console to remotely control the surgical device and comprising a first communication device and a radio frequency (RF) reader;
   a dongle configured to physically couple to the connection port of the surgical console and comprising a second communication device and a passive RF device, wherein the dongle is configured to be powered through the connection port of the surgical console;
   wherein the RF reader of the control device is configured to receive pairing information from the passive RF device of the dongle in response to the passive RF device being within a threshold proximity of the RF reader; and
   wherein the first and second communication devices are configured to wirelessly connect based on the pairing information to thereby enable the control device to wirelessly communicate with the surgical console to remotely control the surgical device.

2. The surgical system of claim 1, wherein, absent the dongle, the connection port of the surgical console is configured to receive a connector of a cable for coupling to the control device.

3. The surgical system of claim 1, wherein the first and second communication devices are configured to wirelessly connect based on the pairing information in response to the dongle being physically coupled to the connection port of the surgical console.

4. The surgical system of claim 1, wherein the pairing information comprises at least a unique identification of the dongle and communication parameters associated with the dongle.

5. The surgical system of claim 1, wherein the dongle is configured to encrypt the pairing information and the control device is configured to decrypt the pairing information.

6. The surgical system of claim 1, wherein the first communication device is configured to transmit control data to the second communication device such that the control device remotely controls the surgical device using the control data, and wherein the control device is configured to encrypt the control data and the dongle is configured to decrypt the control data.

7. The surgical system of claim 1, wherein the control device comprises a housing and wherein the first communication device and RF reader are integrated within the housing.

8. The surgical system of claim 1, wherein the RF reader and the passive RF device are configured to operate on a frequency defined between 30 kHz and 30 MHz, 400 MHz and 450 MHz, or 860 MHz and 960 MHz.

9. The surgical system of claim 1, wherein the first and second communication devices are configured to operate on a frequency greater than 1 GHz.

10. The surgical system of claim 1, wherein the dongle comprises a connector identifier and an adaptive connector, and wherein the connector identifier is configured to determine a type of communication protocol used by the surgical console to receive and transmit data and the adaptive connector is configured to communicate with the surgical console based on the type of the communication protocol used by the surgical console.

11. A method of operating a surgical system, the surgical system comprising a surgical console configured to operate a surgical device and comprising a connection port, a control device configured to communicate with the surgical console to remotely control the surgical device and comprising a first communication device and a radio frequency (RF) reader, and a dongle comprising a second communication device and a passive RF device, the method including steps of:

establishing a threshold proximity between the passive RF device of the dongle and the RF reader of the control device, wherein the control device is disposed in a sterile field and wherein the step of establishing the threshold proximity between the passive RF device of the dongle and the RF reader of the control device comprises a step of moving the dongle into the sterile field, and wherein the control device is further defined as at least one of a foot-operable control device, a hand-operable control device, and a mobile computing device;

receiving, with the RF reader of the control device, pairing information from the passive RF device of the dongle in response to the passive RF device and the RF reader being within the threshold proximity;

physically coupling the dongle to the connection port of the surgical console;

establishing a wireless connection between the first and second communication devices based on the pairing information; and remotely and wirelessly controlling the surgical device with the control device using the wireless connection.

12. The method of claim 11, wherein the dongle comprises no internal power supply and wherein the method further comprises a step of powering the dongle through the connection port.

13. The method of claim 11, further comprising steps of: encrypting the pairing information with the dongle; and decrypting the pairing information with the control device.

14. The method of claim 11, wherein the step of remotely and wireless controlling the surgical device further comprises a step of transmitting, with the control device, control data to the surgical console via the first communication device and wherein the method further comprises steps of:
encrypting the control data with the control device; and
decrypting the control data with the dongle.

15. The method of claim 11, wherein the surgical console is disposed in a non-sterile field, and wherein the method further comprises a step of moving the dongle into the non-sterile field to physically couple the dongle to the connection port of the surgical console.

16. The method of claim 11, wherein the step of receiving pairing information from the passive RF device occurs at a frequency between 30 kHz to 30 MHz.

17. The method of claim 11, wherein the step of receiving pairing information from the passive RF device occurs at a frequency between 300 MHz to 1 GHz.

18. The method of claim 11, wherein the step of establishing the wireless connection between the first and second communication devices occurs at a frequency greater than 300 MHz.

19. The method of claim 11, wherein the control device is further defined as a foot-operable control device.

20. The method of claim 11, wherein the wireless connection is established between the first and second communication devices based on the pairing information in response to the dongle being physically coupled to the connection port of the surgical console.

21. A surgical system comprising:
a surgical console configured to operate a surgical device and comprising a connection port;
a control device configured to communicate with the surgical console to remotely control the surgical device and comprising a connection port;
a first dongle comprising a first communication device and a passive radio frequency (RF) device;
a second dongle comprising a second communication device and an RF reader;
one of the first and second dongles being configured to physically couple to the connection port of the surgical console and the other one of the first and second dongles being configured to physically couple to the connection port of the control device;
wherein the RF reader of the second dongle is configured to receive pairing information from the passive RF device of the first dongle in response to the RF reader and the passive RF device being within a threshold proximity to one another; and
wherein the first and second communication devices are configured to wirelessly connect based on the pairing information to thereby enable the control device to wirelessly communicate with the surgical console to remotely control the surgical device.

22. The surgical system of claim 21, wherein the first dongle is configured to be powered through the connection port of the surgical console.

23. The surgical system of claim 1, wherein the control device is further defined as a foot-operable control device.

24. The surgical system of claim 21, wherein the control device is further defined as a foot-operable control device.

25. The surgical system of claim 21, wherein the first and second communication devices are configured to wirelessly connect based on the pairing information in response to the dongle being physically coupled to the connection port of the surgical console.

* * * * *